US00PP28430P2

(12) United States Plant Patent
van de Pol

(10) Patent No.: US PP28,430 P2
(45) Date of Patent: Sep. 19, 2017

(54) ***CAMPANULA* PLANT NAMED 'PTDB141302'**

(50) Latin Name: *Campanula portenschlagiana*
Varietal Denomination: PTDB141302

(71) Applicant: Peter van de Pol, Twello (NL)

(72) Inventor: Peter van de Pol, Twello (NL)

(73) Assignee: Genius Genes Production Facilities B.V., Twello (NL)

( * ) Notice: Subject to any disclaimer, the term of this patent is extended or adjusted under 35 U.S.C. 154(b) by 0 days.

(21) Appl. No.: 14/998,877

(22) Filed: Feb. 25, 2016

(51) Int. Cl.
*A01H 5/02* (2006.01)

(52) U.S. Cl.
USPC ..... Plt./414

(58) Field of Classification Search
USPC ..... Plt./414
See application file for complete search history.

*Primary Examiner* — Keith Robinson
(74) *Attorney, Agent, or Firm* — C. A. Whealy

(57) ABSTRACT

A new and distinct *Campanula* plant named 'PTDB141302', characterized by its compact, upright to spreading and uniformly mounding plant habit; freely flowering habit; dark violet-colored flowers; and good container and garden performance.

2 Drawing Sheets

Botanical designation: *Campanula portenschlagiana.*
Cultivar denomination: 'PTDB141302'.

BACKGROUND OF THE INVENTION

The present invention relates to a new and distinct *Campanula* plant, botanically known as *Campanula portenschlagiana* and hereinafter referred to by the cultivar name 'PTDB141302'.

The new *Campanula* plant is a product of a planned breeding program conducted by the Inventor in Twello, The Netherlands. The objective of the breeding program is to create new compact and freely-flowering *Campanula* plants that have good container and garden performance.

The new *Campanula* plant originated from a cross-pollination in August, 2012 of a proprietary selection of *Campanula portenschlagiana* identified as code number PTDB-1200201S-PT, not patented, as the female, or seed, parent with a proprietary selection of *Campanula portenschlagiana* identified as code number PTDB-13001103S, not patented, as the male, or pollen, parent. The new *Campanula* plant was discovered and selected by the Inventor as a single flowering plant from within the progeny of the stated cross-pollination grown in a controlled greenhouse environment in Twello, The Netherlands in July, 2013.

Asexual reproduction of the new *Campanula* plant by terminal vegetative cuttings in a controlled greenhouse environment in Twello, The Netherlands, since November, 2013, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PTDB141302'. These characteristics in combination distinguish 'PTDB141302' as a new and distinct *Campanula* plant:

1. Compact, upright to spreading and uniformly mounding plant habit.
2. Freely flowering habit.
3. Dark violet-colored flowers.
4. Good container and garden performance.

Plants of the new *Campanula* differ primarily from plants of the female parent selection in the following characteristics:

1. Plants of the new *Campanula* are more compact than plants of the female parent selection.
2. Plants of the new *Campanula* flower earlier than plants of the female parent selection.

Plants of the new *Campanula* differ primarily from plants of the male parent selection in the following characteristics:

1. Plants of the new *Campanula* are larger than plants of the male parent selection.
2. Plants of the new *Campanula* and the male parent selection differ in flower color as plants of the male parent selection have light purple-colored flowers.

Plants of the new *Campanula* can be compared to plants of *Campanula portenschlagiana* 'Blue Planet', not patented. In side-by-side comparisons conducted in Twello, The Netherlands, plants of the new *Campanula* differ primarily from plants of 'Blue Planet' in the following characteristics:

1. Plants of the new *Campanula* are more compact and more upright than plants of 'Blue Planet'.
2. Flowers of plants of the new *Campanula* are darker in color than flowers of plants of 'Blue Planet'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'PTDB141302' grown in a container.

The photograph on the second sheet is a close-up view of a typical flowering plant of 'PTDB141302'.

DETAILED BOTANICAL DESCRIPTION

Plants used for the aforementioned photographs and following description were grown in 10.5-cm containers during the spring and summer in a glass-covered greenhouse in Poeldijk, The Netherlands and under cultural practices typical of commercial *Campanula* production. During the production of the plants, day temperatures ranged from 18° C. to 28° C., night temperatures ranged from 14° C. to 20° C. and light levels averaged 6,000 lux. Plants were twelve weeks old when the photographs and description were taken. In the following description, color references are made to The Royal Horticultural Society Colour Chart, 2007 Edition, except where general terms of ordinary dictionary significance are used.

Botanical classification: *Campanula portenschlagiana* 'PTDB141302'.

Parentage:

*Female parent*.—Proprietary selection of *Campanula portenschlagiana* identified as code number PTDB-1200201S-PT, not patented.

*Male parent*.—Proprietary selection of *Campanula portenschlagiana* identified as code number PTDB-13001103S, not patented.

Propagation:

*Type*.—By terminal vegetative cuttings.

*Time to initiate roots, summer*.—About ten to twelve days at temperatures about 23° to 24° C.

*Time to initiate roots, winter*.—About seven to ten days at temperatures about 22° to 23° C.

*Time to produce a rooted young plant, summer*.—About 42 days at temperatures about 23° to 24° C.

*Time to produce a rooted young plant, winter*.—About 36 days at temperatures about 22° to 23° C.

*Root description*.—Fine, fleshy; typically white in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Herbaceous perennial; compact, upright to spreading and uniformly mounding plant habit; flattened globular in shape; moderately vigorous growth habit; numerous campanulate flowers positioned above and beyond the foliar plane.

*Plant height*.—About 15.4 cm.

*Plant width*.—About 28.3 cm.

*Lateral branch description*.—Branching habit: Freely branching habit with about 56 lateral branches developing per plant. Length (excluding inflorescences): About 9.1 cm. Diameter: About 2 mm. Internode length: About 1.5 cm. Strength: Moderately strong. Aspect: Upright to horizontal. Texture and luster: Sparsely pubescent; glossy. Color: Close to 144A.

Leaf description:

*Arrangement*.—Alternate, simple.

*Length*.—About 1.7 cm.

*Width*.—About 2.6 cm.

*Shape*.—Broadly reniform.

*Apex*.—Acute.

*Base*.—Reniform to hastate.

*Margin*.—Coarsely dentate.

*Texture and luster, upper surface*.—Glabrous; slightly glossy.

*Texture and luster, lower surface*.—Sparsely to moderately pubescent; matte.

*Venation pattern*.—Pinnate.

*Color*.—Developing leaves, upper surface: Close 137A. Developing leaves, lower surface: Close to 137B. Fully expanded leaves, upper surface: Close to N137A and 147C; venation, close to 143B. Fully expanded leaves, lower surface: Close to 137B; venation, close to 144A.

*Petioles*.—Length: About 3.5 cm. Diameter: About 1 mm. Strength: Strong. Texture and luster, upper and lower surfaces: Glabrous; moderately glossy. Color, upper surface: Close to 144A. Color, lower surface: Close to 144B.

Flower description:

*Flower arrangement and flowering habit*.—Single campanulate flowers arranged in terminal and axillary simple cymes; flowers face mostly upright to outwardly; freely flowering habit with about ten flowers developing in terminal inflorescences and about three flowers developing in axillary inflorescences; about 1,500 flowers develop per plant during the flowering season.

*Natural flowering season*.—Plants begin flowering about ten weeks after planting; relatively long flowering period, plants flower continuously from mid-May into August in The Netherlands.

*Flower longevity on the plant*.—About ten days; flowers persistent.

*Fragrance*.—None detected.

*Flower buds*.—Length: About 1.2 cm. Diameter: About 3 mm. Shape: Narrowly oblong. Color: Close to N88B; longitudinal ribs, close to 85C.

*Inflorescence height*.—About 4.4 cm.

*Inflorescence diameter*.—About 3.7 cm.

*Flower diameter*.—About 2.2 cm.

*Flower depth (height)*.—About 1.6 cm.

*Petals*.—Quantity and arrangement: Typically five per flower, arranged in a single whorl; lower 60% of the petal is fused. Length: About 1.8 cm. Width: About 6 mm. Shape: Narrowly elliptic to narrowly obovate; free parts, slightly recurved. Apex: Broadly acute. Margin: Entire. Texture and luster, upper surface: Glabrous; matte. Texture and luster, lower surface: Glabrous; slightly glossy. Color: When opening, upper surface: Close to N87A; tubular stripes, close to N87D. When opening, lower surface: Close to N87A. Fully opened, upper surface: Slightly darker than N87A; tubular stripes, close to N87C; color does not change with development. Fully opened, lower surface: Close to N87B.

*Sepals*.—Quantity and arrangement: Typically five per flower, arranged in a single whorl; lower 20% of the sepal is fused. Length: About 6.5 mm. Width: About 1.5 mm. Shape: Lanceolate. Apex: Narrowly acute. Margin: Entire. Texture and luster, upper and lower surfaces: Glabrous; matte. Color: When opening, upper surface: Close to 146A to 146B. When opening, lower surface: Close to 143C. Fully opened, upper surface: Close to 146A. Fully opened, lower surface: Close to 143C.

*Peduncles*.—Length: About 1.9 cm. Diameter: About 1.5 mm. Aspect, flowers in terminal inflorescences: Mostly upright. Aspect, flowers in axillary inflorescences: About 35° from lateral branch axis. Strength: Moderately strong. Texture and luster: Slightly ribbed, glabrous; moderately glossy. Color: Close to 144B.

*Pedicels*.—Length: About 9 mm. Diameter: About 1 mm. Aspect: About 35° from peduncle axis. Strength: Moderately strong. Texture and luster: Glabrous; moderately glossy. Color: Close to 144B.

*Reproductive organs*.—Stamens: Quantity: Typically five per flower. Filament length: About 2 mm. Filament color: Close to NN155D. Anther length: About 4 mm. Anther shape: Lanceolate. Anther color: Close to 8C. Pollen amount: Moderate. Pollen color: Close to 4C to 4D. Pistils: Quantity per flower: One. Pistil length: About 1 cm. Stigma shape: Three-parted, decurrent. Stigma color: Close to NN88D. Style length: About 8.5 mm. Style color: Close to between 86A and N88A. Ovary color: Close to 143C.

*Seeds and fruits*.—Seed and fruit production has not been observed on plants of the new *Campanula*.

Pathogen & pest resistance: Plants of the new *Campanula* have not been noted to be resistant to pathogens and pests common to *Campanula* plants.

Garden performance: Plants of the new *Campanula* have exhibited good garden performance and to tolerant to rain, wind, high temperatures about 35° C. and to be hardy to USDA Hardiness Zone 3.

It is claimed:

1. A new and distinct *Campanula* plant named 'PTDB141302' as illustrated and described.

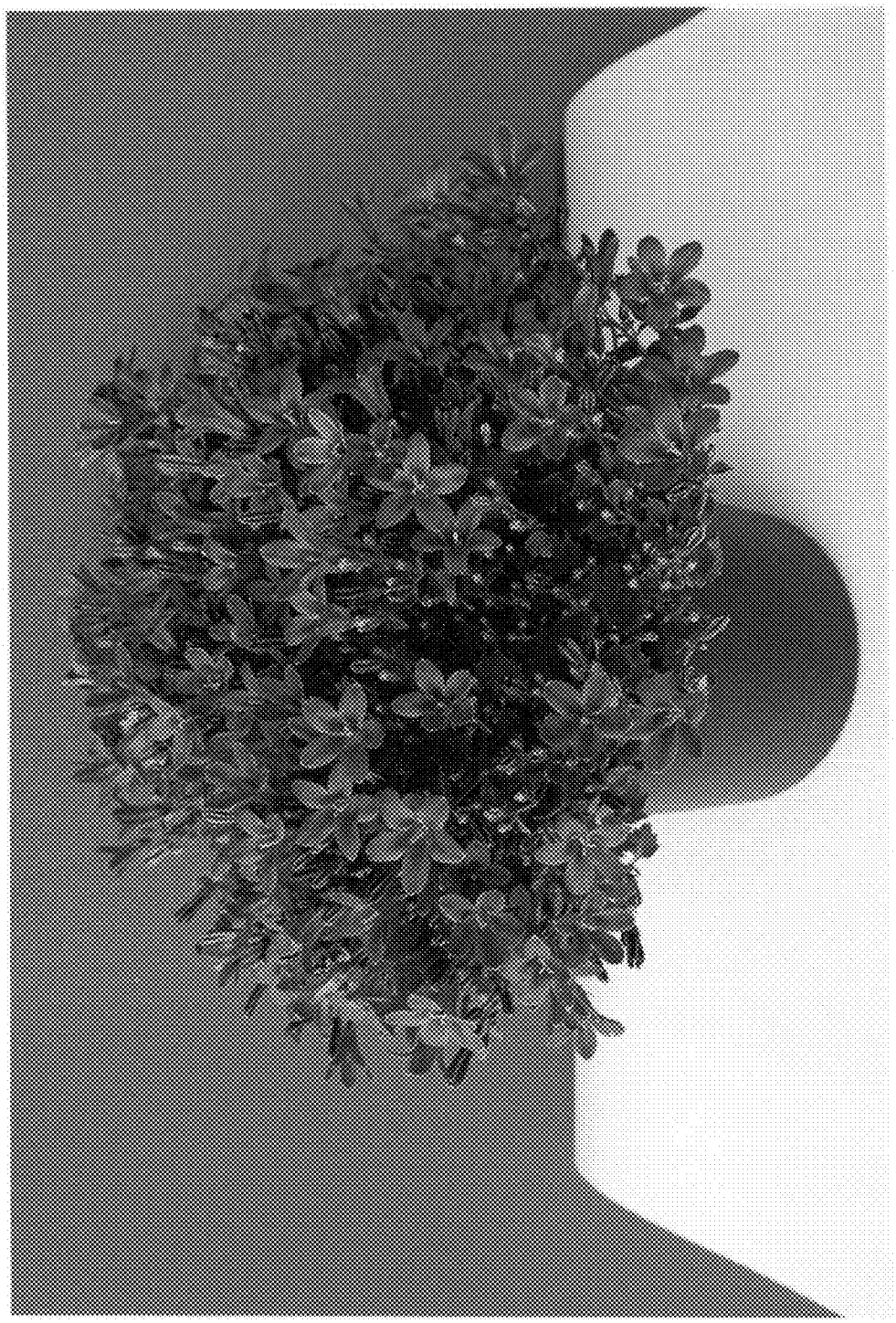

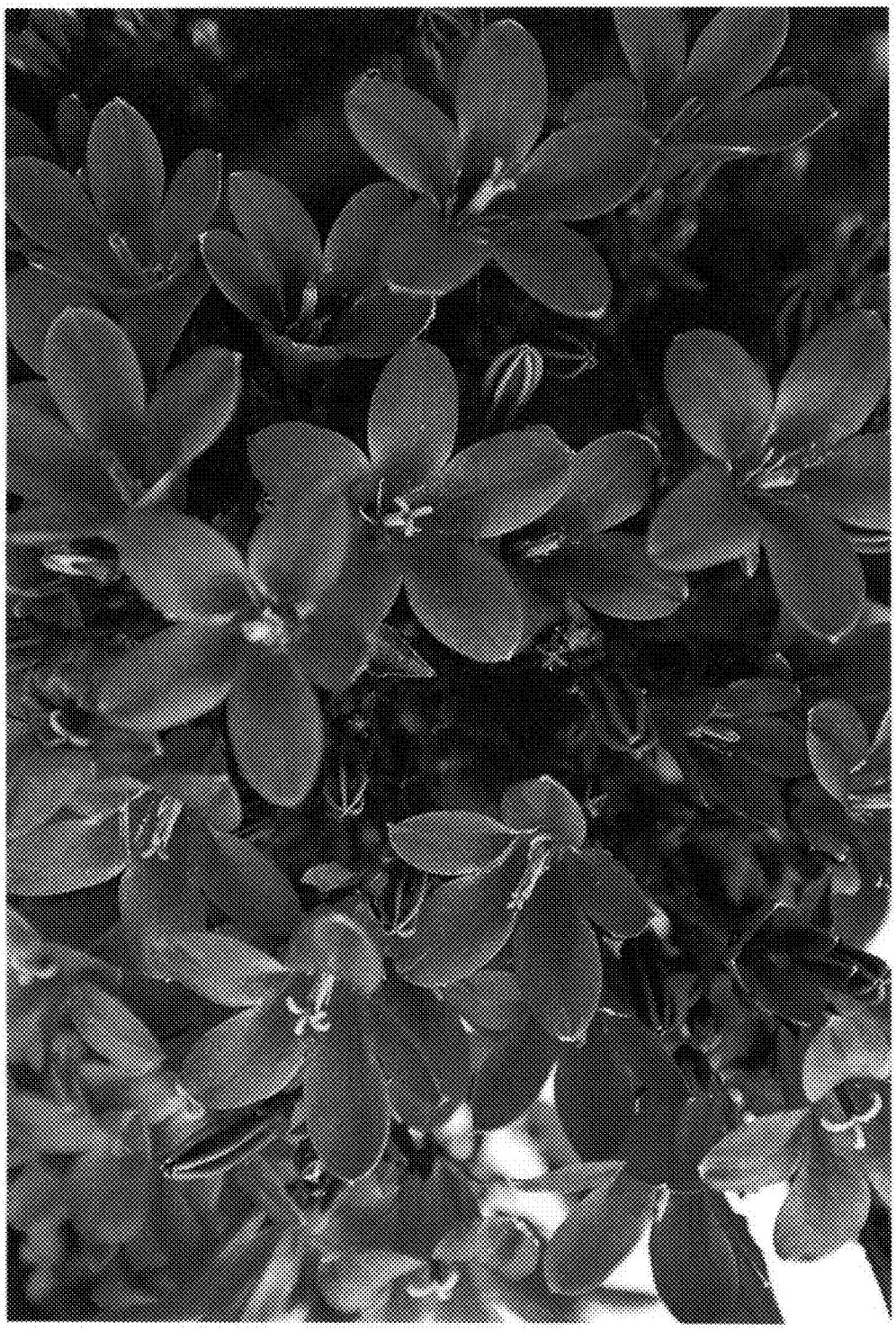

* * * * *